United States Patent
Cao et al.

(10) Patent No.: US 11,617,555 B2
(45) Date of Patent: Apr. 4, 2023

(54) APPARATUS FOR BLOOD SUGAR LEVEL DETECTION

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 17/863,613

(22) Filed: Jul. 13, 2022

(65) Prior Publication Data
US 2022/0354448 A1  Nov. 10, 2022

Related U.S. Application Data

(63) Continuation of application No. PCT/CN2020/076911, filed on Feb. 27, 2020.

(51) Int. Cl.
A61B 6/00 (2006.01)

(52) U.S. Cl.
CPC .......... *A61B 6/5217* (2013.01); *A61B 6/4241* (2013.01); *A61B 6/504* (2013.01)

(58) Field of Classification Search
CPC . A61B 5/14532; A61B 6/4241; A61B 6/4452; A61B 6/504; A61B 6/5217
See application file for complete search history.

(56) References Cited

U.S. PATENT DOCUMENTS

2009/0074139 A1* 3/2009 Hempel ............ A61B 5/14532
600/407

FOREIGN PATENT DOCUMENTS

| CN | 103713448 A | 4/2014 |
|---|---|---|
| CN | 103767724 A | 5/2014 |
| CN | 106691486 A | 5/2017 |
| CN | 107115122 A | 9/2017 |
| CN | 107374645 A | 11/2017 |
| CN | 107533146 A | 1/2018 |
| CN | 108271415 A | 7/2018 |
| CN | 109561841 A | 4/2019 |
| TW | 201406348 A | 2/2014 |
| TW | 201625925 A | 7/2016 |
| WO | 9827865 A1 | 7/1998 |
| WO | 2015162215 A1 | 10/2015 |
| WO | 2019080041 A1 | 5/2019 |

* cited by examiner

*Primary Examiner* — Manuchehr Rahmjoo
(74) *Attorney, Agent, or Firm* — IPro, PLLC; Qian Gu

(57) ABSTRACT

Disclosed herein is an apparatus comprising: an X-ray source configured to direct X-rays through a human tissue; an X-ray detector configured to capture an image of the human tissue with the X-rays; wherein the apparatus is configured to identify an image of a blood vessel from the image of the human tissue and configured to determine a blood sugar level based on the image of the blood vessel.

20 Claims, 12 Drawing Sheets

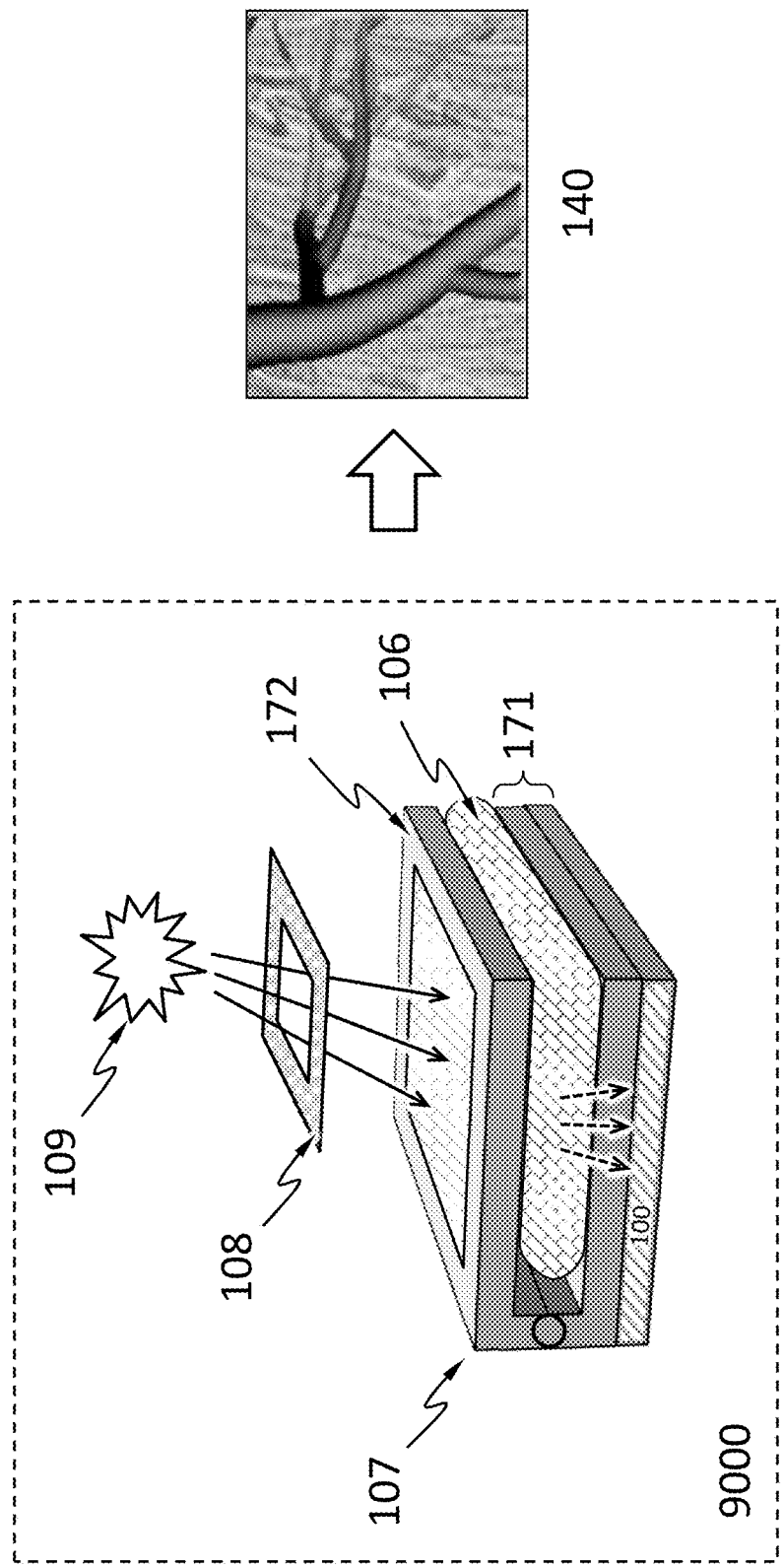

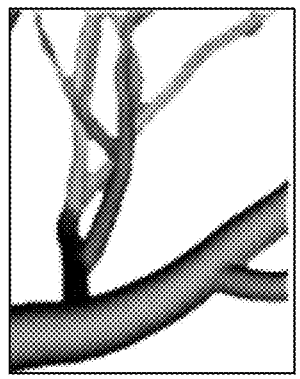
141
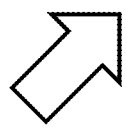
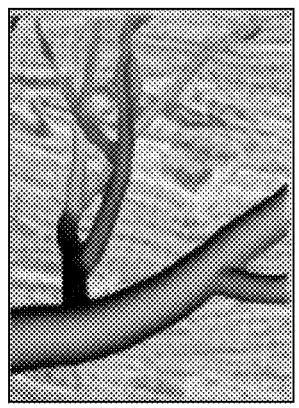
140
Fig. 2A

APPARATUS FOR BLOOD SUGAR LEVEL DETECTION

BACKGROUND

X-ray detectors may be devices used to measure the flux, spatial distribution, spectrum or other properties of radiations.

X-ray detectors may be used for many applications. One important application is imaging. Radiation imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor X-ray detectors largely overcome this problem by direct conversion of radiation into electric signals. A semiconductor X-ray detector may include a semiconductor layer that absorbs radiation in wavelengths of interest. When a radiation particle is absorbed in the semiconductor layer, multiple charge carriers (e.g., electrons and holes) are generated and swept under an electric field towards electric contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is an apparatus comprising: an X-ray source configured to direct X-rays through a human tissue; an X-ray detector configured to capture an image of the human tissue with the X-rays; wherein the apparatus is configured to identify an image of a blood vessel from the image of the human tissue and configured to determine a blood sugar level based on the image of the blood vessel.

In an aspect, the apparatus is configured to determine the blood sugar level based on the image of the blood vessel by determining attenuation of the X-rays by the blood vessel from the image of the blood vessel.

In an aspect, the apparatus is configured to determine the blood sugar level based on the image of the blood vessel by a temporal change of the attenuation.

In an aspect, the X-rays have photon energies no more than 10 keV.

In an aspect, the X-rays have photon energies in a range of 6 keV to 9 keV.

In an aspect, the apparatus further comprises a filter configured to prevent a portion of the X-rays that has photon energies outside a predetermined range from reaching the human tissue.

In an aspect, the apparatus further comprises a clamp comprising a first arm and a second arm and configured to compress the human tissue between the first arm and the second arm.

In an aspect, the X-ray detector is in the first arm.

In an aspect, the second arm is not opaque to the X-rays.

In an aspect, the clamp is configured to compress the human tissue to a fixed thickness.

In an aspect, the X-ray detector comprises: an X-ray absorption layer comprising an electric contact; a first voltage comparator configured to compare a voltage of the electric contact to a first threshold; a second voltage comparator configured to compare the voltage to a second threshold; a counter configured to register a number of photons of the X-rays incident on the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number of the photons to increase by one, when the second voltage comparator determines that an absolute value of the voltage equals or exceeds an absolute value of the second threshold.

In an aspect, the controller is configured to activate the second voltage comparator at a beginning or expiration of the time delay.

In an aspect, the controller is configured to connect the electric contact to an electrical ground.

In an aspect, a rate of change of the voltage is substantially zero at expiration of the time delay.

In an aspect, the X-ray absorption layer comprises a diode.

In an aspect, the X-ray absorption layer comprises silicon, germanium, GaAs, CdTe, CdZnTe, or a combination thereof.

In an aspect, the X-ray detector does not comprise a scintillator.

In an aspect, the human tissue is an earlobe or abductor pollicis.

Disclosed herein is a method comprising: capturing a first image of a human tissue by exposing the human tissue to X-rays, at a first point in time; identifying a first image of a blood vessel from the first image of the human tissue; capturing a second image of the human tissue by exposing the human tissue to X-rays, at a second point in time later than the first point in time; identifying a second image of the blood vessel from the second image of the human tissue; determining a blood sugar level at the second point in time based on the second image of the blood vessel and the first image of the blood vessel.

In an aspect, the human tissue has the same thickness at the first point in time and at the second point in time.

In an aspect, a blood sugar level at the first point in time is known.

In an aspect, determining the blood sugar level at the second point in time is based on a difference between attenuation of the X-rays by the blood vessel measured from the second image of the blood vessel and attenuation of the X-rays by the blood vessel measured from the first image of the blood vessel.

In an aspect, the X-rays have photon energies no more than 10 keV.

BRIEF DESCRIPTION OF FIGURES

FIG. 1 schematically shows an apparatus, according to an embodiment.

FIG. 2A shows an example of determining the attenuation from the image of the blood vessel.

DETAILED DESCRIPTION

Figure 2B:
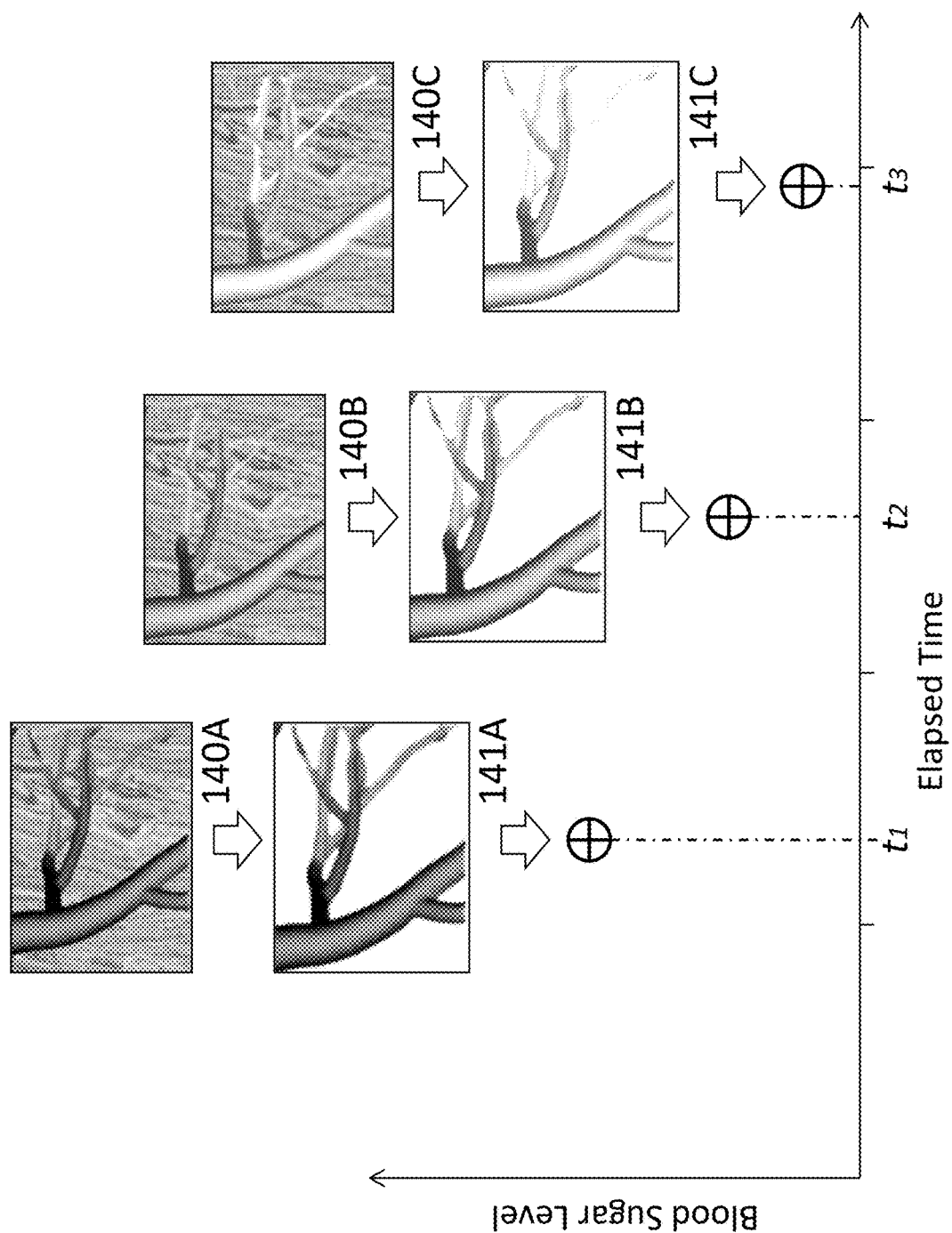
FIG. 2B schematically shows a chart of temporal changes of blood sugar levels determined from images of the blood vessel, according to an embodiment.

FIG. 1 schematically shows an apparatus 9000 comprising an X-ray source 109, an X-ray detector 100, according to an embodiment. The X-ray source 109 may be configured to generate X-rays and direct the X-rays through a human tissue 106. The X-rays may have photo energies no more than 10 keV (e.g., in a range of 6 keV to 9 keV). As shown in FIG. 1, the apparatus 9000 may further include a filter 108 configured to prevent a portion the X-rays that has photon energies outside a predetermined range (e.g., outside the range 6 keV to 9 keV) from reaching the human tissue 106. The human tissue 106 may be an earlobe, an adductor pollicis, or the other suitable tissue. The apparatus 9000 may further include a clamp 107, as schematically shown in the example of FIG. 1. The clamp 107 has a first arm 171 and a second arm 172. The clamp 107 is configured to compress the human tissue 106 between the first arm 171 and the second arm 172. The clamp 107 may compress the human tissue 106 to a fixed thickness. For example, when the clamp 107 is closed, the first arm 171 and the second arm 172 are spaced apart by a fixed distance. The X-ray detector 100 may be in the first arm 171, as shown in FIG. 1. The second arm 172 may be not opaque to the X-rays so that the X-rays from the X-ray source 109 may pass through the second arm 172 to reach the human tissue 106. For example, the second arm 172 may have at least a portion that is not opaque to the X-rays.

The X-ray detector 100 is configured to capture an image 140 of the human tissue 106 with the X-rays that passes through the human tissue 106, according to an embodiment. The apparatus 9000 may be configured to identify an image (e.g., image 141 in FIG. 2A) of a blood vessel from the image 140, and to determine a blood sugar level based on the image of the blood vessel. The blood sugar in the blood vessel may affect the interaction of the blood vessel with the X-rays. For example, the blood vessel with a higher blood sugar level may attenuate the X-rays more strongly. The apparatus 9000 may determine the attenuation of the X-rays by the blood vessel from the image of the blood vessel and determine the blood sugar level using the attenuation.

FIG. 2A shows an example of determining the attenuation from the image of the blood vessel. The pixels in the image 140 of the human tissue 106 that do not cover any portion of the blood vessel are discarded. The remaining pixels of the image 140 constitute the image 141 of the blood vessel. The sum of the values of intensity of the pixels of the image 141 (i.e., the remaining pixels of the image 140) is calculated. This sum is a representation of the attenuation of the X-rays by the blood vessel.

Determining the blood sugar level using the attenuation may include using a temporal change of the attenuation, for example, from a baseline attenuation, the blood sugar level associated with which is known. In an example shown in FIG. 2B, a plurality of images (e.g., 141A, 1416, 141C) of the blood vessel are identified by the apparatus 9000 from images of the human tissue 106 captured at different points in time (images 140A, 1406, 140C). For example, image 141A of the blood vessel is identified from the image 140A of the human tissue captured at point $t_1$ in time; image 1416 of the blood vessel is identified from the image 1406 of the human tissue captured at point $t_2$ in time; image 141C of the blood vessel is identified from the image 140C of the human tissue captured at point $t_3$ in time. The blood sugar level at point $t_1$ in time may be known. Based on the temporal changes of the attenuation determined from the image 1416 and 141C relative to the attenuation determined from image 141A, the blood sugar levels at point $t_2$ in time and point $t_3$ in time may be determined.

Figure 3A:
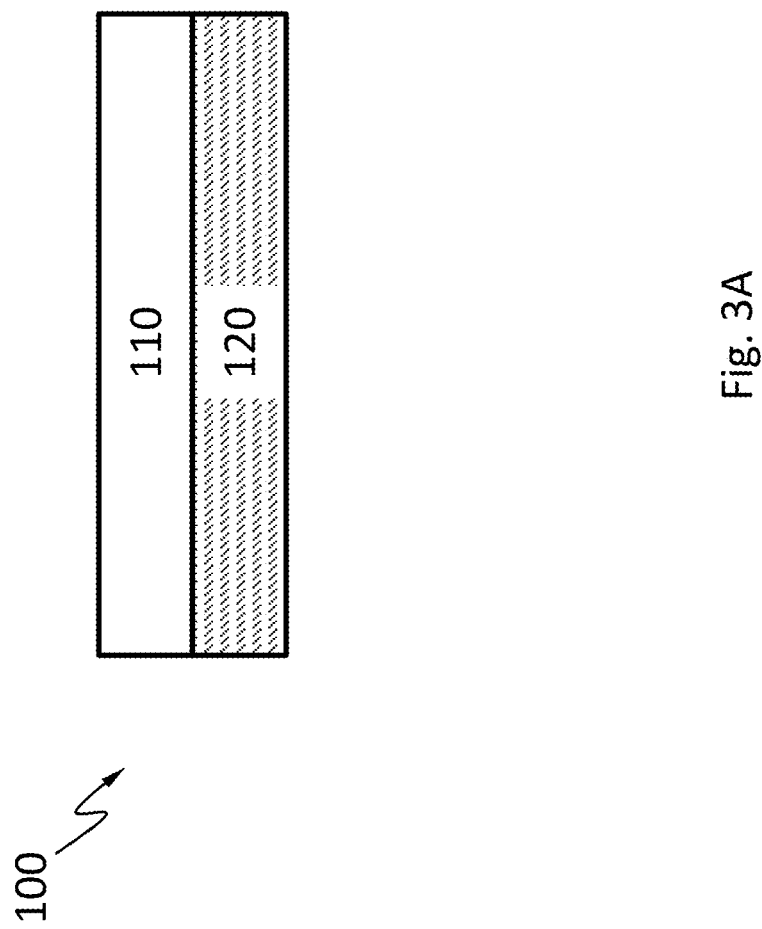
FIG. 3A schematically shows a cross-sectional view of an X-ray detector, according to an embodiment.

FIG. 3A schematically shows a cross-sectional view of the X-ray detector 100, according to an embodiment. The detector 100 may include an X-ray absorption layer 110 and an electronics layer 120 (e.g., an ASIC) for processing or analyzing electrical signals incident X-ray generates in the X-ray absorption layer 110. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest. The X-ray detector 100 does not include a scintillator, according to an embodiment.

Figure 3B:
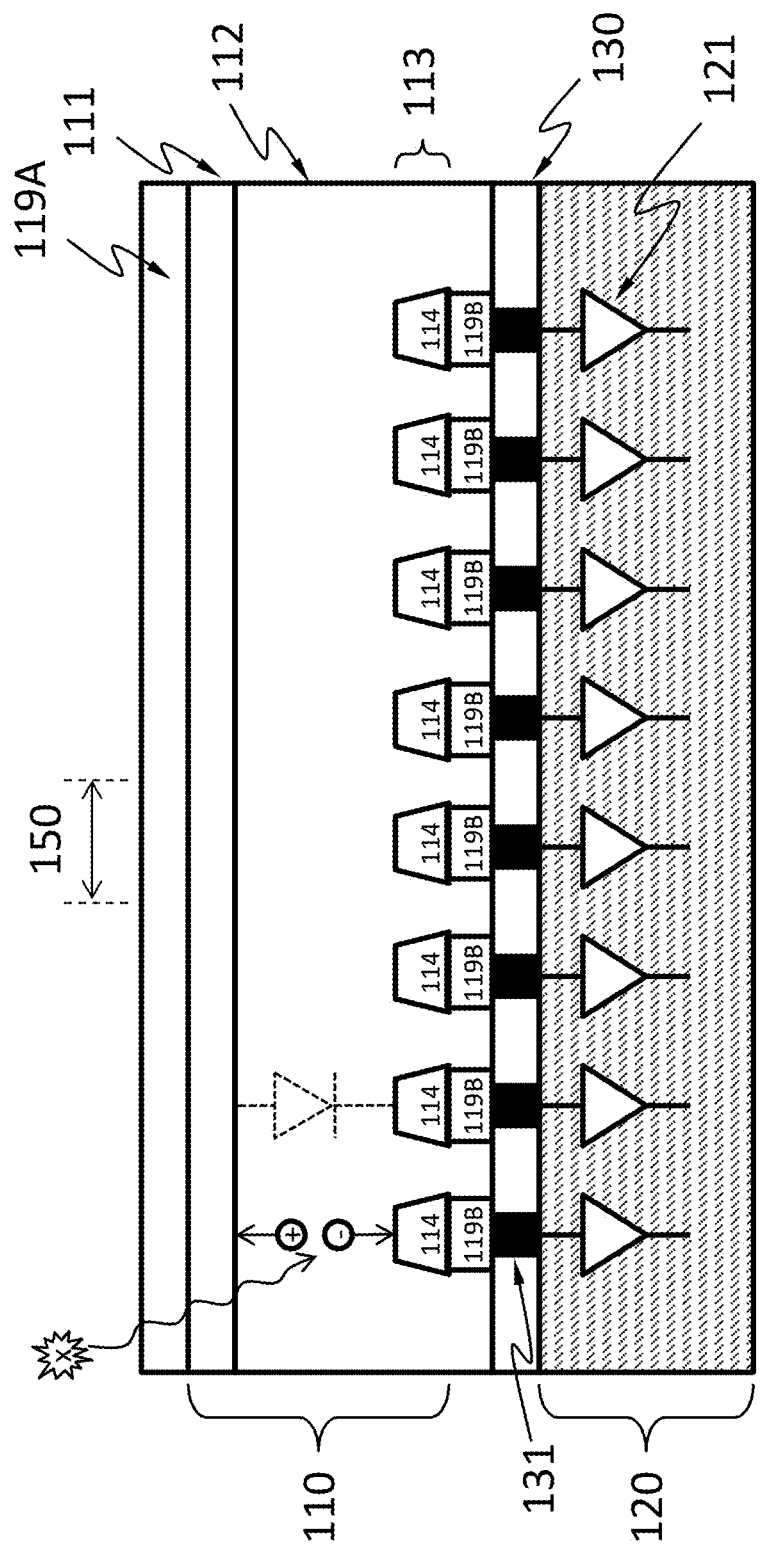
FIG. 3B schematically shows a detailed cross-sectional view of the X-ray detector, according to an embodiment.

As shown in a detailed cross-sectional view of the detector 100 in FIG. 3B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 3B, each of the discrete regions 114 of the second doped region 113 forms a diode with the first doped region 111 and the optional intrinsic region 112. Namely, in the example in FIG. 3B, the X-ray absorption layer 110 has a plurality of diodes having the first doped region 111 as a shared electrode. The first doped region 111 may also have discrete portions.

When a photon of X-ray hits the X-ray absorption layer 110 including diodes, the photon of X-ray may be absorbed and generate one or more charge carriers by a number of mechanisms. A photon of X-ray may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single photon of X-ray are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a photon of X-ray incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a photon of X-ray incident therein flow to the discrete region 114. Namely, less than 2%, less than 1%, less than 0.1%, or less than 0.01% of these charge carriers flow beyond the pixel.

Figure 3C:
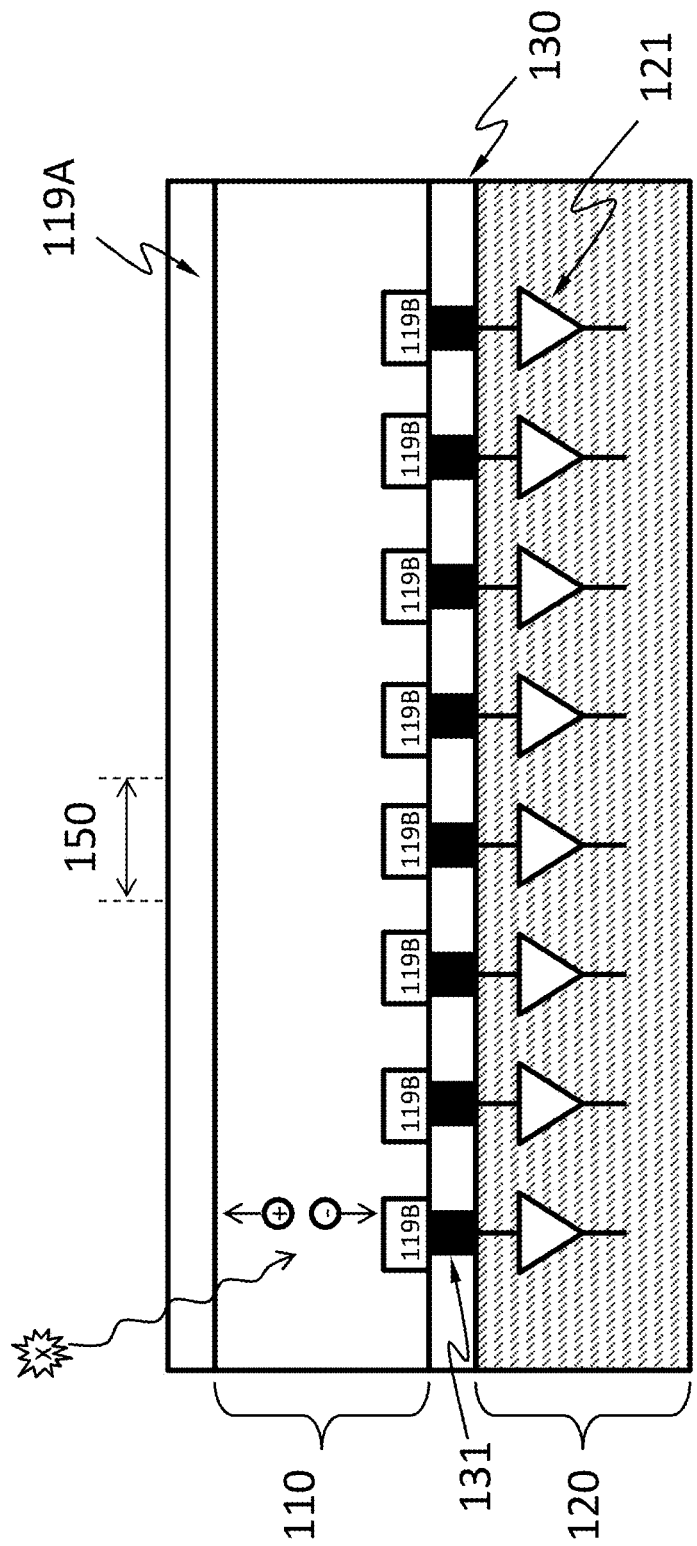
FIG. 3C schematically shows an alternative detailed cross-sectional view of the X-ray detector, according to an embodiment.

As shown in an alternative detailed cross-sectional view of the detector 100 in FIG. 3C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When a photon of X-ray hits the X-ray absorption layer 110 including a resistor but not diodes, it may be absorbed and generate one or more charge carriers by a number of mechanisms. A photon of X-ray may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single photon of X-ray are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a photon of X-ray incident around the footprint of one of these discrete portions of the electrical contact 119B are not substantially shared with another of these discrete portions of the electrical contact 119B. The pixel 150 associated with a discrete portion of the electrical contact 119B may be an area around the discrete portion in which substantially all (more than 98%, more than 99.5%, more than 99.9% or more than 99.99% of) charge carriers generated by a photon of X-ray incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by photons of X-ray incident on the X-ray absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 4A:
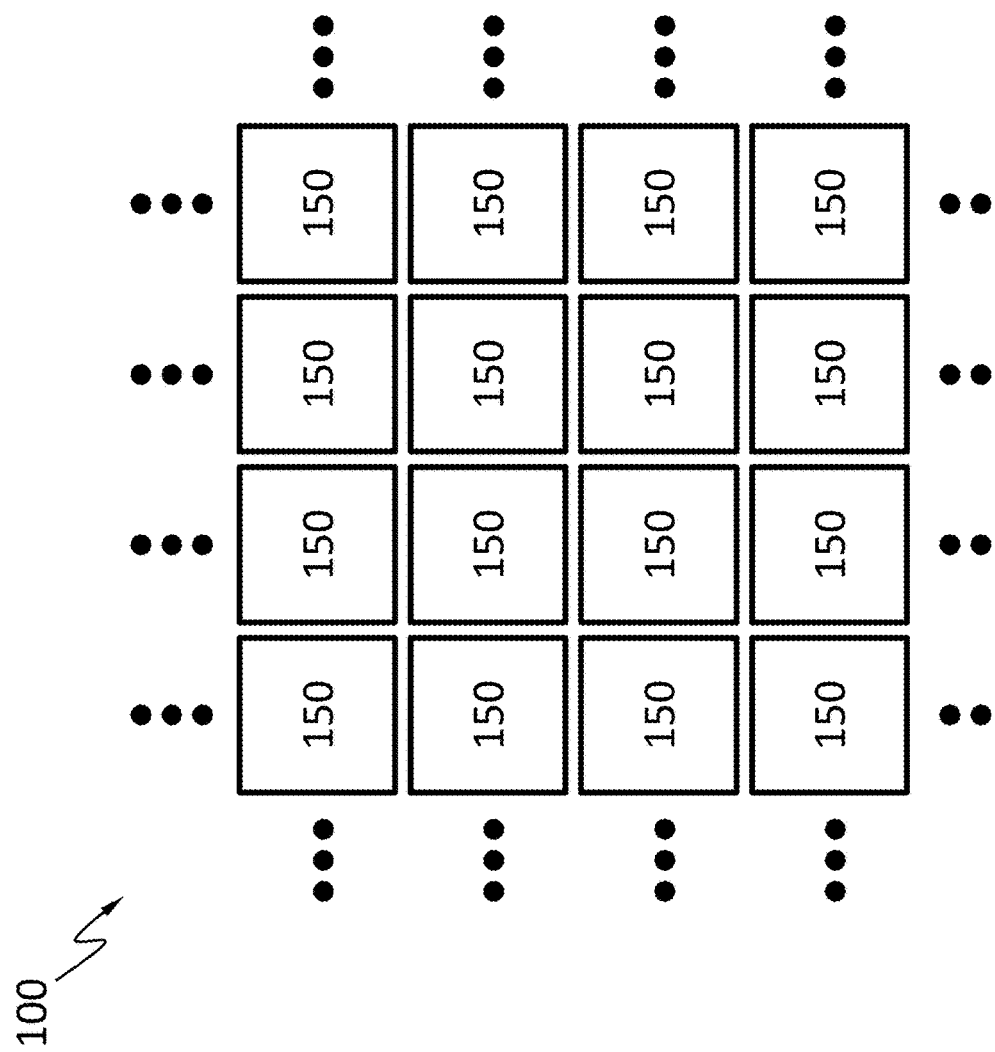
FIG. 4A schematically a top view of a portion of the X-ray detector, according to an embodiment.

FIG. 4A schematically a top view of a portion of the X-ray detector 100 with an array of pixels 150, according to an embodiment. The array may be a rectangular array, a honeycomb array, a hexagonal array or any other suitable array. Each pixel 150 may be configured to detect a photon of X-ray incident thereon and determine the energy of the photon of X-ray. All the pixels 150 may be configured to detect and count the numbers of the photons of X-ray incident thereon within a plurality of bins of energy within the same period of time. Each pixel 150 may have its own analog-to-digital converter (ADC) configured to digitize an analog signal representing the energy of an incident photon of X-ray into a digital signal. For X-ray imaging applications, an ADC with a 10-bit resolution or higher is useful. Each pixel 150 may be configured to measure its dark current, such as before or concurrently with each photon of X-ray incident thereon. Each pixel 150 may be configured to deduct the contribution of the dark current from the energy of the photon of X-ray incident thereon. The pixels 150 may be configured to operate in parallel. For example, when one pixel 150 measures an incident photon of X-ray, another pixel 150 may be waiting for a photon of X-ray to arrive. The pixels 150 may not have to be individually addressable.

The X-ray detector 100 may have at least 100, 2500, 10000, or more pixels 150. The detector 100 may be configured to add the numbers of photons of X-ray for the bins of the same energy range counted by a subset of all the pixels 150 (e.g., the pixels covering the blooding vessel). For example, the detector 100 may add the numbers the pixels 150 stored in a bin for energy from 6 KeV to 7 KeV, add the numbers the pixels 150 stored in a bin for energy from 8 KeV to 9 KeV, and so on. In one embodiment, the photons of X-rays transmitted through the human tissue 106 whose energies are within a range are counted and added into in related bins. The X-ray detector 100 may compile the added numbers for the bins as a spectrum of intensity of the photons of X-ray incident on the X-ray detector 100.

Figure 4B:
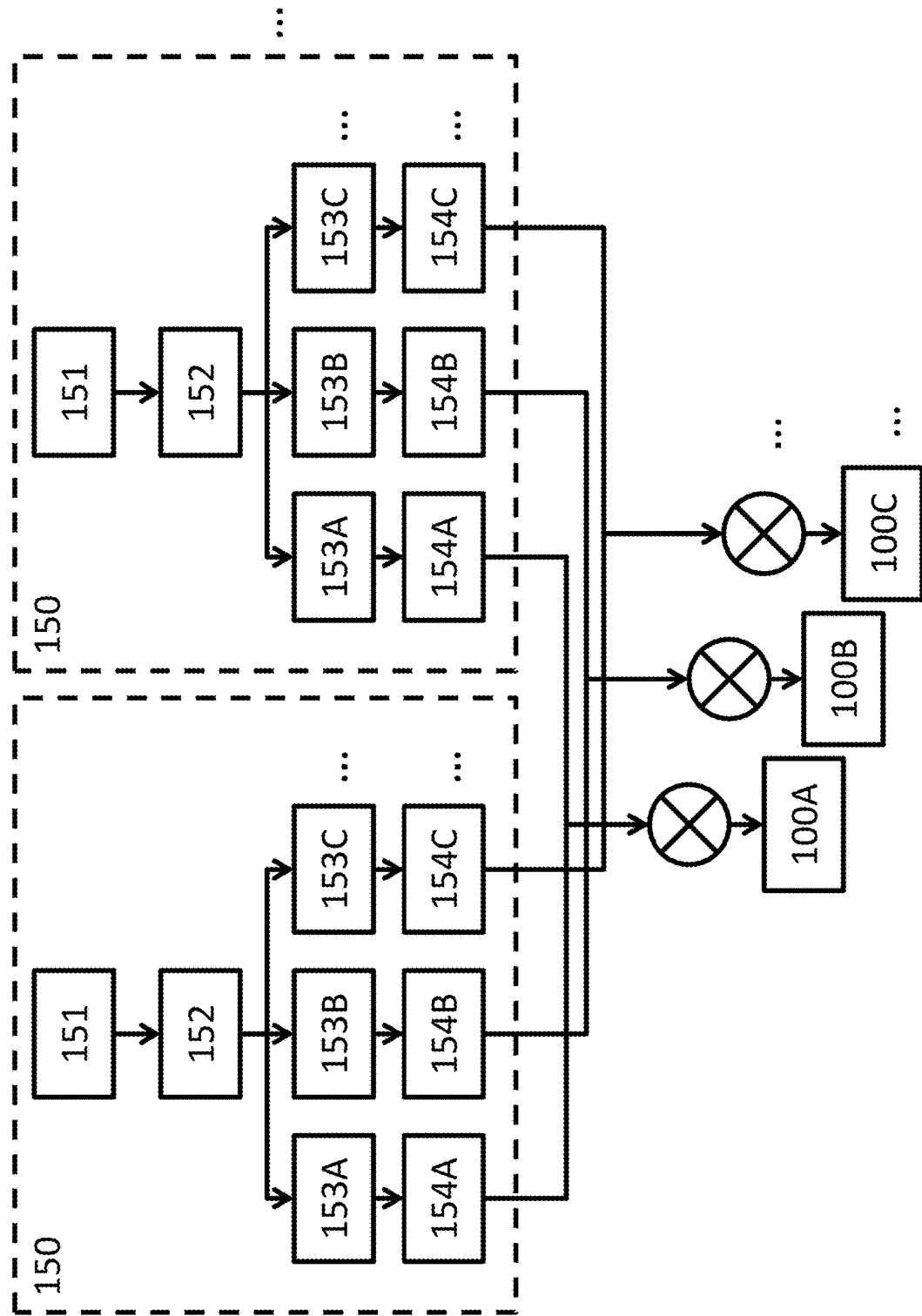
FIG. 4B schematically shows a block diagram for the X-ray detector, according to an embodiment.

FIG. 4B schematically shows a block diagram for the detector 100, according to an embodiment. Each pixel 150 may measure the energy 151 of a photon of X-ray incident thereon. The energy 151 of the photon of X-ray is digitized in step 152 into one of a plurality of bins 153A, 153B, 153C . . . . The bins 153A, 153B, 153C . . . each have a corresponding counter 154A, 154B and 154C, respectively. When the energy 151 is allocated into a bin, the number stored in the corresponding counter increases by one. The detector 100 may added the numbers stored in all the counters corresponding to bins for the same energy range in the subset of pixels 150. For example, the numbers stored in all the counters 154C in the subset of pixels 150 may be added and stored in a global counter 100C for the same energy range. The numbers stored in all the global counters may be compiled into an energy spectrum of the X-ray incident on the detector 100.

Figure 5A:
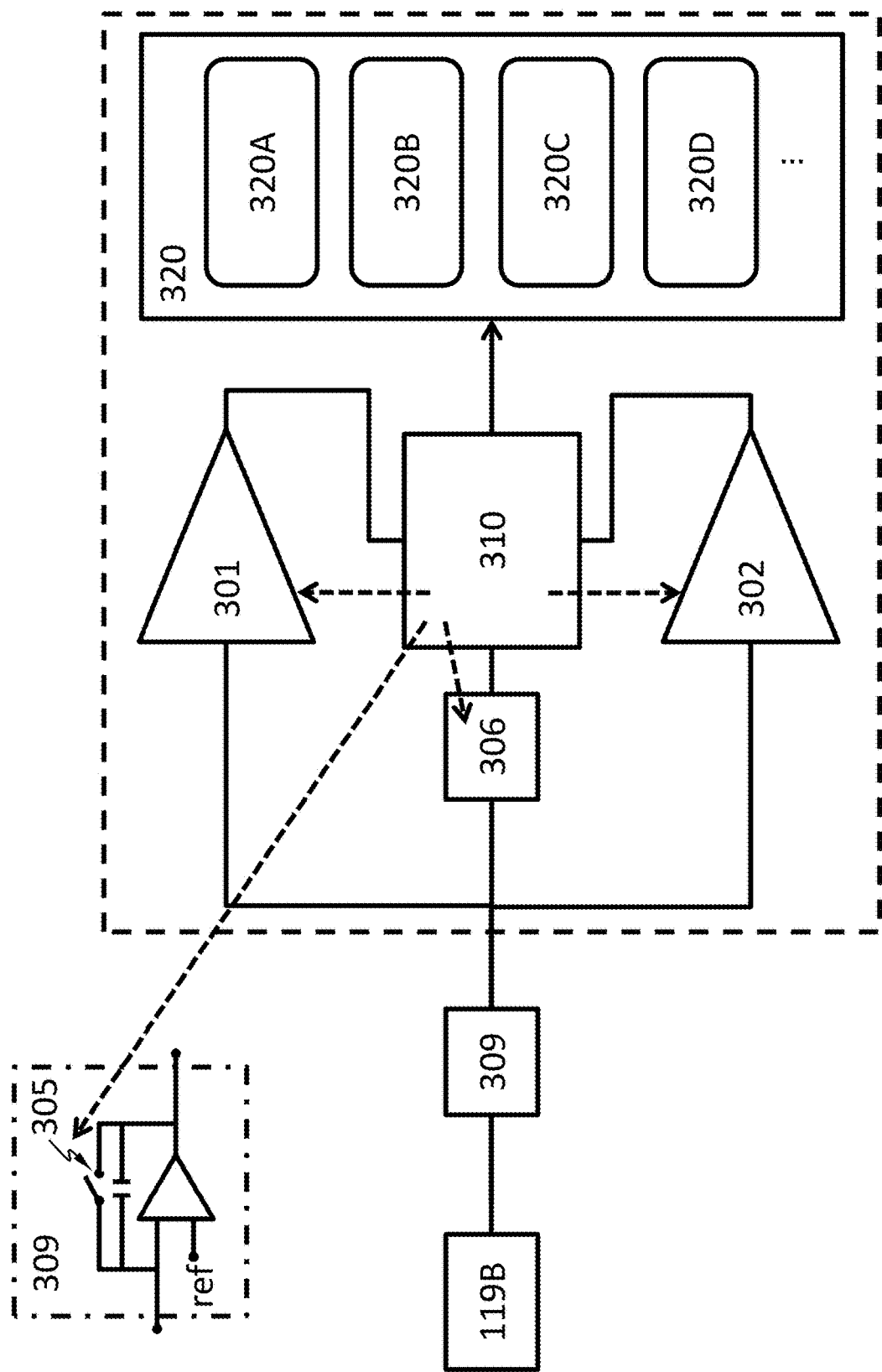
FIG. 5A-FIG. 5B each schematically show a component diagram of an electronic system of the X-ray detector, according to an embodiment.
Figure 5B:
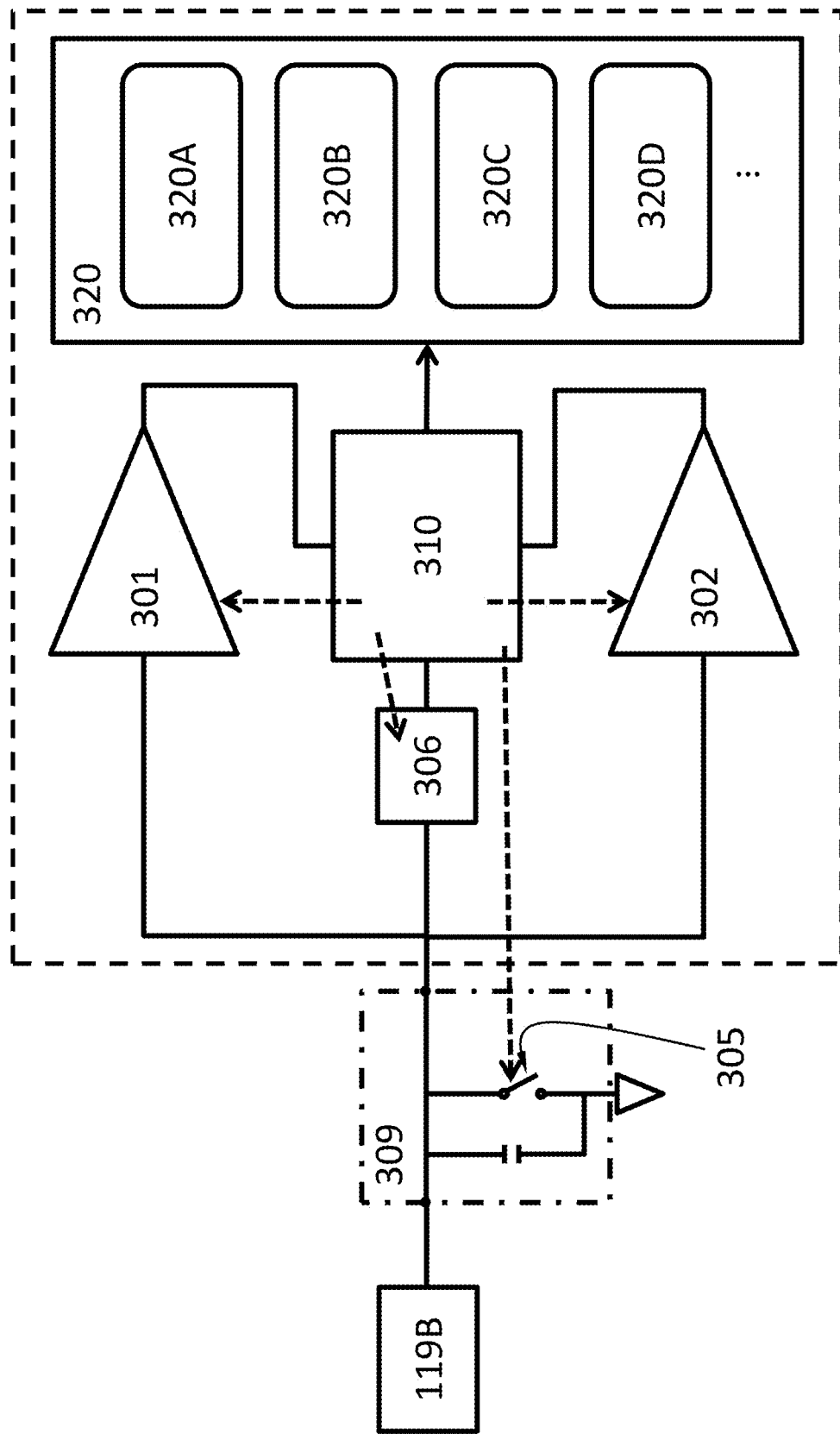

FIG. 5A and FIG. 5B each show a component diagram of the electronic system 121, according to an embodiment. The electronic system 121 may include a first voltage comparator 301, a second voltage comparator 302, a plurality of counters 320 (including counters 320A, 320B, 320C, 320D . . . ), a switch 305, an optional voltmeter 306, an integrator 309 and a controller 310.

The first voltage comparator 301 is configured to compare the voltage of at least one of the electric contacts 119B to a first threshold, according to an embodiment. The first voltage comparator 301 may be configured to monitor the voltage directly, or to calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident photon of X-ray may generate on the electric contact 119B. The maximum voltage may depend on the energy of the incident photon of X-ray, the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident photon of X-ray may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident photons of X-ray. However, having a high speed is often at the cost of power consumption.

The counter 320 is configured to register at least a number of photons of X-ray incident on the pixel 150. The counter 320 may be a software component (e.g., a number stored in a computer memory) or a hardware component (e.g., a 4017 IC and a 7490 IC). In an embodiment, the counter 320 of each pixel is associated with a plurality of bins for an energy range. For example, counter 320A may be associated with a bin for particles with energy of 6-7 KeV, counter 320B may be associated with a bin for 7-8 KeV, counter 320C may be associated with a bin for 8-9 KeV, counter 320D may be associated with a bin for 9-10 KeV. When the energy of an incident photon of X-ray is determined by the to be in the bin the counter 320 is associated with, the number registered in the bin of counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold), according to an embodiment. The absolute value may be used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include the integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 6:
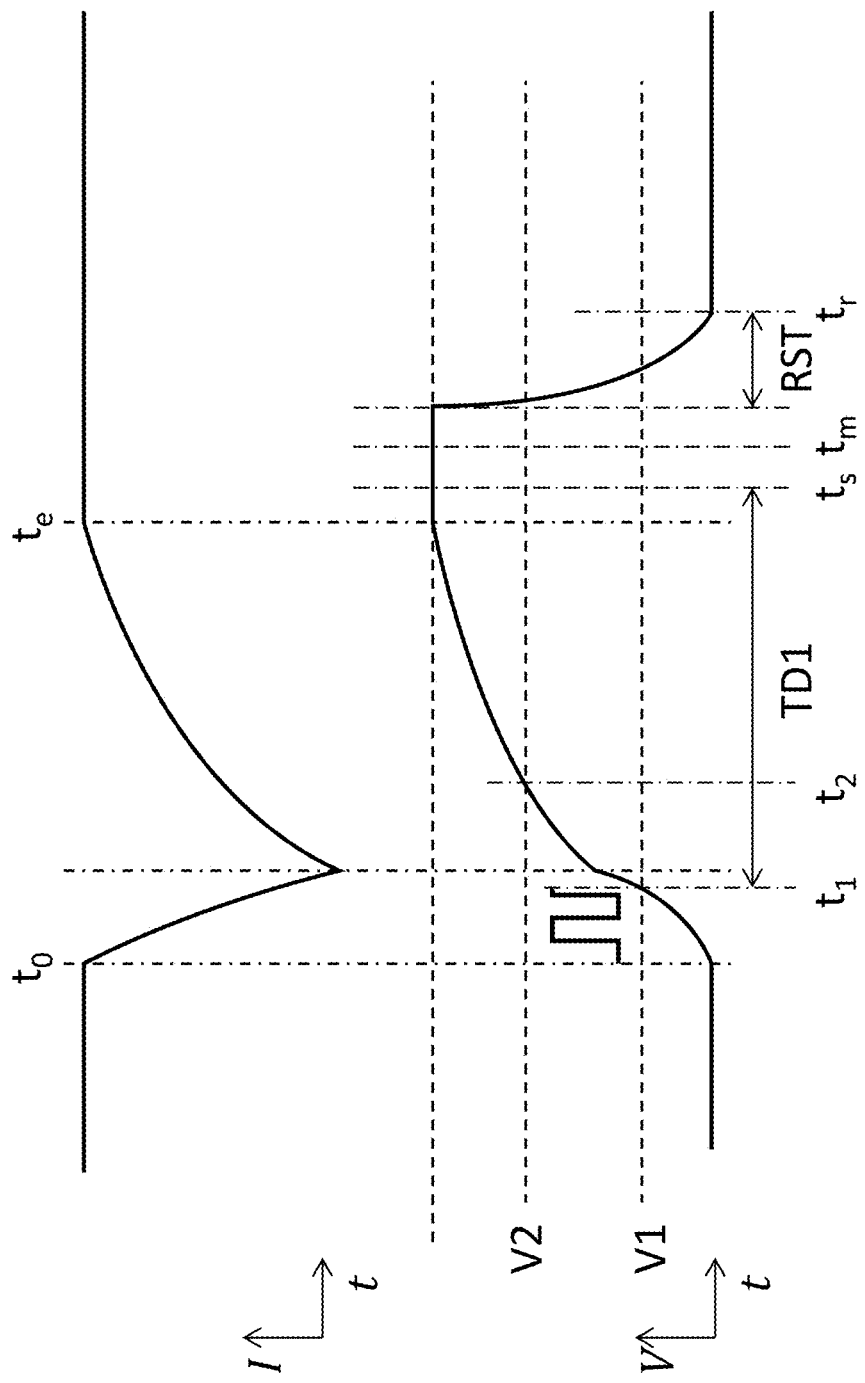
FIG. 6 schematically shows a temporal change of an electric current caused by charge carriers generated by an incident photon of X-ray, and a corresponding temporal change of a voltage, according to an embodiment.

FIG. 6 schematically shows a temporal change of the electric current flowing through the electric contact 119B (upper curve) caused by charge carriers generated by a photon of X-ray incident on the pixel 150 encompassing the electric contact 119B, and a corresponding temporal change of the voltage of the electric contact 119B (lower curve). The voltage may be an integral of the electric current with respect to time. At time to, the photon of X-ray hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the photon of X-ray drift out of the X-ray absorption layer 110. At time $t_s$, the time delay TD1 expires. At or after time $t_e$, the controller 310 causes the voltmeter 306 to digitize the voltage and determines which bin the energy of the photon of X-ray falls in. The controller 310 then causes the number registered by the counter 320 corresponding to the bin to increase by one. In the example of FIG. 6, time $t_s$ is after time $t_e$; namely TD1 expires after all charge carriers generated by the photon of X-ray drift out of the X-ray absorption layer 110. If time $t_e$ cannot be easily measured, TD1 can be empirically chosen to allow sufficient time to collect essentially all charge carriers generated by a photon of X-ray but not too long to risk have another incident photon of X-ray. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the photon of X-ray, which relates to the energy of the photon of X-ray. The controller 310 may be configured to determine the energy of the photon of X-ray, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident photon of X-ray. If the first voltage comparator 301 has been deactivated, the controller 310 can activate it at any time before RST expires. If the controller 310 has been deactivated, it may be activated before RST expires.

Figure 7:
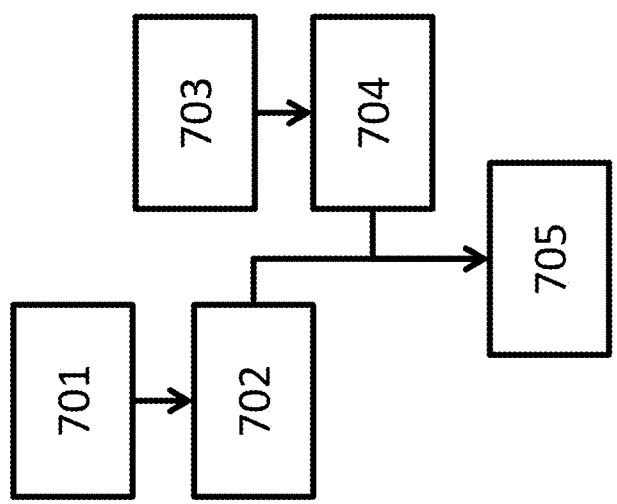
FIG. 7 shows a flowchart for a method, according to an embodiment.

FIG. 7 shows a flowchart for a method, according to an embodiment. In procedure 701, a first image of the human tissue 106 is captured by exposing the human tissue 106 to X-rays, at a first point in time. In procedure 702, a first image of the blood vessel is identified from the first image of the human tissue 106. In procedure 703, a second image of the human tissue 106 is captured by exposing the human tissue 106 to X-rays, at a second point in time later than the first point in time. In procedure 704, a second image of the blood vessel is identified from the second image of the human tissue 106. In procedure 705, a blood sugar level at the second point in time is determined based on the second image of the blood vessel and the first image of the blood vessel. The human tissue 106 may have the same thickness at the first point in time and at the second point in time. The blood sugar level at the first point in time may be known. Determining the blood sugar level at the second point in time may be based on a difference between attenuation of the X-rays by the blood vessel measured from the second image of the blood vessel and attenuation of the X-rays by the blood vessel measured from the first image of the blood vessel.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
an X-ray source configured to direct X-rays through a human tissue;
an X-ray detector configured to capture an image of the human tissue with the X-rays;
wherein the apparatus is configured to identify an image of a blood vessel from the image of the human tissue and configured to determine a blood sugar level based on the image of the blood vessel;
wherein the apparatus is configured to determine the blood sugar level based on the image of the blood vessel by determining attenuation of the X-rays by the blood vessel from the image of the blood vessel;
wherein the apparatus is configured to determine the attenuation based on a sum of values of intensity of pixels of the image of the blood vessel;
wherein the apparatus is configured to determine the blood sugar level based on the image of the blood vessel by a temporal change of the attenuation.

2. The apparatus of claim 1, wherein the X-rays have photon energies no more than 10 keV.

3. The apparatus of claim 1, wherein the X-rays have photon energies in a range of 6 keV to 9 keV.

4. The apparatus of claim 1, further comprising a filter configured to prevent a portion of the X-rays that has photon energies outside a predetermined range from reaching the human tissue.

5. The apparatus of claim 1, further comprising a clamp comprising a first arm and a second arm and configured to compress the human tissue between the first arm and the second arm.

6. The apparatus of claim 5, wherein the X-ray detector is in the first arm.

7. The apparatus of claim 5, wherein the second arm is not opaque to the X-rays.

8. The apparatus of claim 5, wherein the clamp is configured to compress the human tissue to a fixed thickness.

9. The apparatus of claim 1, wherein the X-ray detector comprises:
an X-ray absorption layer comprising an electric contact;
a first voltage comparator configured to compare a voltage of the electric contact to a first threshold;
a second voltage comparator configured to compare the voltage to a second threshold;
a counter configured to register a number of photons of the X-rays incident on the X-ray absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number of the photons to increase by one, when the second voltage comparator determines that an absolute value of the voltage equals or exceeds an absolute value of the second threshold.

10. The apparatus of claim 9, wherein the controller is configured to activate the second voltage comparator at a beginning or expiration of the time delay.

11. The apparatus of claim 9, wherein the controller is configured to connect the electric contact to an electrical ground.

12. The apparatus of claim 9, wherein a rate of change of the voltage is substantially zero at expiration of the time delay.

13. The apparatus of claim 9, wherein the X-ray absorption layer comprises a diode.

14. The apparatus of claim 9, wherein the X-ray absorption layer comprises silicon, germanium, GaAs, CdTe, CdZnTe, or a combination thereof.

15. The apparatus of claim 1, wherein the X-ray detector does not comprise a scintillator.

16. The apparatus of claim 1, wherein the human tissue is an earlobe or abductor pollicis.

17. A method comprising:
capturing a first image of a human tissue by exposing the human tissue to X-rays, at a first point in time;
identifying a first image of a blood vessel from the first image of the human tissue;
capturing a second image of the human tissue by exposing the human tissue to X-rays, at a second point in time later than the first point in time;
identifying a second image of the blood vessel from the second image of the human tissue;
determining a blood sugar level at the second point in time based on the second image of the blood vessel and the first image of the blood vessel;
wherein determining the blood sugar level at the second point in time is based on a difference between attenuation of the X-rays by the blood vessel measured from the second image of the blood vessel and attenuation of the X-rays by the blood vessel measured from the first image of the blood vessel;
wherein the attenuation of the X-rays by the blood vessel measured from the first image of the blood vessel is determined based on a sum of values of intensity of pixels of the first image of the blood vessel;
wherein the attenuation of the X-rays by the blood vessel measured from the second image of the blood vessel is determined based on a sum of values of intensity of pixels of the second image of the blood vessel.

18. The method of claim 17, wherein the human tissue has the same thickness at the first point in time and at the second point in time.

19. The method of claim 17, wherein a blood sugar level at the first point in time is known.

20. The method of claim 17, wherein the X-rays have photon energies no more than 10 keV.

* * * * *